United States Patent [19]
Nelson

[11] Patent Number: 5,284,468
[45] Date of Patent: Feb. 8, 1994

[54] ORTHOPEDIC SPLINTING ARTICLE

[75] Inventor: Thomas W. Nelson, Lenexa, Kans.

[73] Assignee: M-Pact Worldwide Management Corporation, Eudora, Kans.

[21] Appl. No.: 746,909

[22] Filed: Aug. 19, 1991

[51] Int. Cl.$^5$ ............................................. A61F 5/00
[52] U.S. Cl. ........................................... 602/5; 602/8
[58] Field of Search ............... 128/89 R, 90, 91 R, 128/155, 156, 157, 87 R; 525/61, 56, 57; 602/4, 7, 8, 5

[56] References Cited

U.S. PATENT DOCUMENTS

| | | | |
|---|---|---|---|
| 2,194,579 | 3/1940 | Wedger | 128/90 |
| 2,277,259 | 3/1942 | Schnabel | 128/90 |
| 2,282,274 | 5/1942 | Weiswasser | 128/90 |
| 2,609,347 | 9/1952 | Wilson. | |
| 2,616,418 | 11/1952 | Eberl | 128/90 |
| 2,653,917 | 9/1953 | Hammon. | |
| 2,664,367 | 12/1955 | Wilson. | |
| 2,668,153 | 12/1956 | Hammon. | |
| 2,846,407 | 8/1958 | Wilson. | |
| 2,847,992 | 8/1958 | Leeds | 128/90 |
| 3,663,470 | 5/1972 | Nishimura et al.. | |
| 3,737,398 | 5/1973 | Yamaguchi et al.. | |
| 3,849,238 | 11/1974 | Gould et al.. | |
| 4,052,282 | 10/1977 | Rubushiro | 128/90 |
| 4,066,488 | 1/1978 | von der Lehr | 128/90 |
| 4,098,728 | 7/1978 | Rosenblatt. | |
| 4,539,369 | 9/1985 | Duckwall | 525/61 |
| 4,664,662 | 5/1987 | Webster | 602/47 |
| 4,801,636 | 1/1989 | Smith | 525/61 |
| 4,852,556 | 8/1989 | Groiso | 128/89 R |
| 5,053,455 | 10/1991 | Kroggel | 525/61 |

OTHER PUBLICATIONS

Kanebo, Product Brochure, PVA Sponge, general heading "Chemical Resistance", pp. 19-20.

*Primary Examiner*—Michael A. Brown
*Attorney, Agent, or Firm*—Shook, Hardy & Bacon

[57] ABSTRACT

A polyvinyl acetal sponge formed from a high molecular weight polyvinyl alcohol is used for forming a splint for a portion of body, such as during healing of a bone fracture or other injury. The sponge is maintained in a softened condition in the presence of vapors of a softening agent such as ethyl alcohol within a sealed pouch. Upon removal from the pouch, the sponge is applied to the body portion and it hardens to form the splint as the softening agent vapors dissipate.

18 Claims, 1 Drawing Sheet

ORTHOPEDIC SPLINTING ARTICLE

BACKGROUND OF THE INVENTION

This invention relates in general to orthopedic splints and, more particularly, to synthetic splints and packaged splints.

Many types of splints are available for orthopedic purposes such as to immobilize body portions to allow a broken bone or other injury to heal. Some of the more common types of splints include those made from plaster-of-paris, metals, high temperature plastics, low temperature plastics, and synthetic materials.

Plaster-of-paris splints are perhaps the most widely utilized splints because of their low cost and their ability to conform to the contours of the underlying body portion. Despite their widespread usage, plaster splints suffer from a number of deficiencies. Application of plaster splints can be messy since water must be used to activate the chemical reaction which results in curing of the plaster-of-paris material. Such splints also present a risk of burning the underlying skin surface because of the heat generated by the exothermic curing reaction. In order to reduce the risk of burning, the plaster is typically formulated to generate less heat by setting more slowly than would otherwise be desired, such as when rapid immobilization of the injured body portion is needed. Plaster also has a relatively low strength and the resulting splint tends to be very bulky in order to achieve the necessary strength, particularly when used to immobilize a patient's leg.

Splints made from metal and high temperature plastics require the use of special tools for forming and shaping the splint prior to application. While splints resulting from such materials are considerably stronger and more durable than plaster splints, they are significantly more costly than plaster types. Because of their high cost and the special tools required for their application, metal and high temperature plastics splints are generally unsuited for general usage.

The use of splints made from low temperature plastics is also limited by the need for a hot plate or tray of hot water to soften the plastic material prior to application. In addition to the inconvenience presented by such heating, the hot plastic presents a burn hazard to both the technician and the patient. Furthermore, the plastic material does not permit ventilation of the skin surface and maceration of the skin surface can occur.

Synthetic splints, typically layers of fiberglass cloth coated with a water-activated polyurethane resin and applied to a padding material, are quite strong and durable but are considerably more expensive and are less conformable in comparison to plaster. Synthetic splints, like plaster splints, may be unsuited for emergency usage because they require water for activation. The water which is absorbed into the padding also provides an ideal environment for bacterial growth and can cause maceration of the underlying skin, particularly when the splint is worn for an extended period of time. Moreover, the patient is placed at risk by the exothermic curing process which can generate sufficient heat to cause burning or irritation of the patient's skin. The patient and technician must also be protected from contact with the polyurethane resin during application of the splint because the resin is difficult to remove from clothing and skin surfaces.

While synthetic splints of the type described are considerably lighter than those formed from plaster, they are still heavy and bulky and contribute to patient discomfort. The edges of the splint can produce hard, needle-like structures which can abrade and pierce the skin, resulting in further discomfort and injury to the patient. Furthermore, the durability of the cured splint is limited since it is prone to delamination under stress and the fiberglass material has poor fatigue characteristics which can lead to cracking and breaking of the material under repeated loadings. Such splints are also costly to manufacture because a nitrogen environment must be provided for the assembly process. In addition, splints of this type have a limited storage life as they lose their effectiveness over a relatively short period of time.

Another type of synthetic splint which has been developed utilizes a polyvinyl acetal sponge material. The sponge material is provided in rigid preshaped configurations which are then softened in a steam chest for application to the corresponding body portion. The sponge material then returns to its hardened state after drying. While such splints provide a generally acceptable structure of relatively low strength, the requirement of a steam chest to soften the splint for application restricts the use of the splints to locations in which such a device is present. Moreover, the time required to soften and then reharden the splint often is undesirably long, particularly when rapid immobilization of the injured body portion is required, and further limits the suitable uses for the splint. Great care must also be exercised to ensure that the patient is not burned by the heated splint after it is removed from the steam chest.

Because the polyvinyl acetal sponge material of the type described does not soften sufficiently to readily conform to the contours of the underlying body part, the splint must be manufactured to a rigid preformed configuration which approximates the shape of the body portion to which it is to be applied. The use of steam to soften the splint then allows the splint to more closely conform to the body portion. A large stock of splints of various configurations, however, must be maintained in order to ensure that the needed configuration is available for use.

SUMMARY OF THE INVENTION

It is an object of this invention to provide a splint which will set to form a high strength structure but which does not require the use of water in the setting process so that use of the splint is not restricted to areas where a supply of water is available.

It is also an object of this invention to provide a splint which will set to form a high strength structure but which does not require the use of water in the setting process so that the potential for skin maceration as a result of water contacting the skin for an extended period of time is eliminated.

It is another object of this invention to provide a splint which is maintained in a soft and conformable condition by a softening agent which also provides a disinfecting environment upon application of the splint to a body portion so that the risk of infection or skin maceration following application of the splint is greatly reduced.

It is a further object of this invention to provide a synthetic splint which forms a high strength structure having high fatigue strength and impact resistance but which is lighter and less bulky than most conventional splints so that patient comfort is greatly increased.

It is a still further object of this invention to provide a synthetic splint which rapidly forms a high strength structure upon application to a body portion but which is readily conformably to the contours of the body portion so that patient comfort is increased and a more effective splint is provided.

It is yet another object of this invention to provide a synthetic splint which rapidly forms a high strength structure but which does not generate or require heat during either the setting or application process so that there is no risk of the splint burning the skin surface to which it is applied.

It is still another object of this invention to provide a splint package which contains a softened synthetic splint which rapidly forms a high strength structure upon removal from the package so that the splint is readily available for use immediately upon removal from the package.

It is a still further object of this invention to provide a sealed splint package which contains a softened synthetic splint which may be maintained in the package for an extended period of time, even at elevated temperatures, without appreciable degradation so that after long term storage the splint still rapidly forms a high strength structure upon removal from the package.

It is also a further object of this invention to provide a synthetic splint of a strength comparable with or exceeding many conventional types of high strength materials but which has no sharp edges and is easily modified following setting so that patient comfort is greatly improved.

It is also another object of this invention to provide a synthetic splint which is of a comparatively small thickness so that it may be readily cut to the desired shape and which does not utilize multiple layers of splinting material so that it may be quickly applied without the delays which would otherwise result from smoothing out wrinkles and ensuring that multiple splinting layers are in contact with each other.

To accomplish these and other related objects of the invention, in one aspect the invention relates to a splint for use in forming a support structure for a portion of a body, said splint comprising:

a layer of a polyvinyl acetal sponge material made from a high molecular weight polyvinyl alcohol and characterized in that it softens when placed in contact with vapors of a softening agent to permit placement about said body portion and then sets to a hardened state to form said support structure upon exposure to air and dissipation of said vapors.

In another aspect, the invention pertains to a packaged splint for use in forming a hard support structure about a body portion, said packaged splint comprising:

a layer of a polyvinyl acetal sponge;

vapors associated with said sponge for softening the sponge to permit placement thereof about said body portion; and a package sealingly enclosing said sponge to maintain the softening agent in association with the sponge, said package being constructed to permit removal of the softened sponge from the package for placement about said body portion, whereupon said sponge sets to a hardened state to form said splint as the softening agent vapors disassociate from the sponge.

BRIEF DESCRIPTION OF THE DRAWINGS

In the accompanying drawings which form a part of the specification and are to be read in conjunction therewith.

DESCRIPTION OF THE PREFERRED EMBODIMENT

Figure 1:
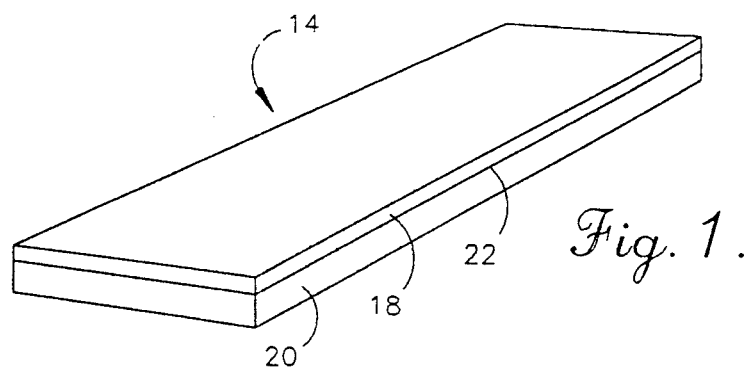
FIG. 1 is a top perspective view of a splint made in accordance with the present invention.
Figure 2:
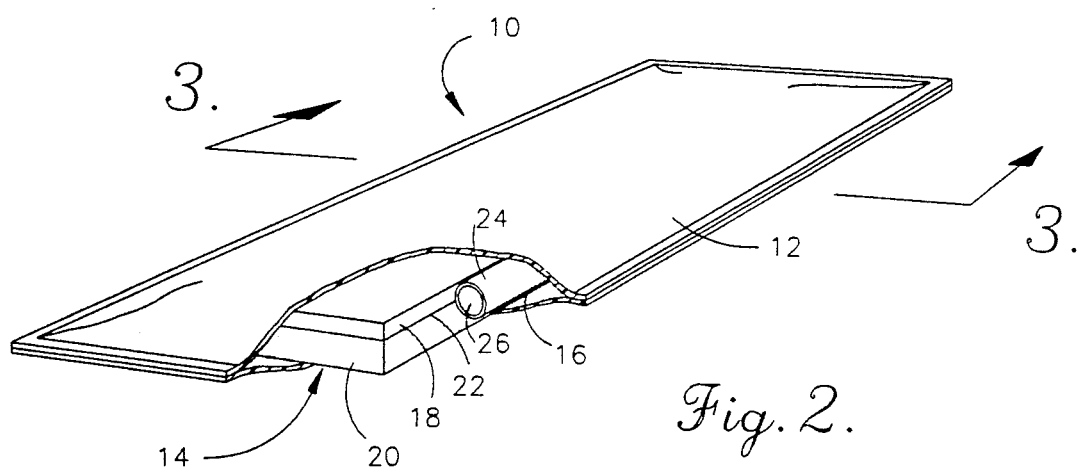
FIG. 2 is a top perspective view of a packaged splint made in accordance with the present invention, with a portion of a pouch broken away to show the splint of FIG. 1 maintained within the pouch.
Figure 3:
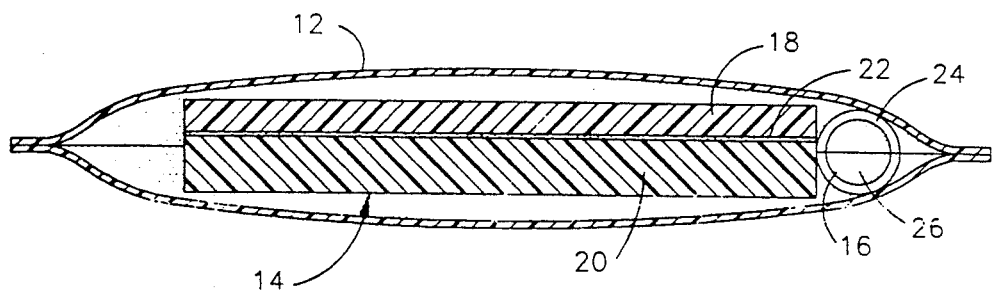
FIG. 3 is an enlarged side elevational view of the packaged splint taken in vertical section along line 3—3 of FIG. 2.

Referring now to the drawings in greater detail, a packaged splint of the present invention is represented broadly by the numeral 10. Packaged splint 10 comprises a sealed pouch 12 in which is contained a synthetic splint 14 in association with a softening agent vapor 16. As used herein, the term "splint" is intended to encompass casts and other types of support structures used to immobolize body parts, including those intended to be used for extended periods of time. Pouch 12 may be formed from any of a variety of suitable materials which are impermeable to vapor 16. Advantageously, the pouch may be formed from various plastics without the need for a foil lining. The pouch is sized to accommodate the splint 14, which may be provided in a continuous roll from which an appropriately sized portion is cut as needed or the splint may be provided in single use sizes. The pouch should be resealable when the splint is in roll form but it may be of a disposable tear open construction when the splint is sized for single use.

Synthetic splint 14 comprises a layer of a polyvinyl acetal sponge 18 which is coupled with a layer of a padding material 20 such as through the use of an adhesive 22, stitching or other suitable methods of associating the sponge with the padding material. The padding material 20 comprises a permeable open-cell foam such as polyurethane foam, although other suitable materials, preferably those which are permeable to the softening agent vapor 16, may be used instead. The thickness of the padding material may be varied as desired to suit particular applications. The padding material 20, in addition to providing a cushion and ventilation for the underlying skin surface, facilitates dissipation of the softening agent vapor 16 from the sponge 18 following application of the splint 14 to a body portion.

The layers of sponge 18 and padding material 20 preferably are of the same length and width, with the dimensions chosen for the desired application. The layers may be provided in the form of a continuous roll of material from which a particularly sized portion may be cut and the package resealed or the layers may be precut to the general size needed for particular uses.

The polyvinyl acetal sponge 18 used in the present invention must soften when associated with an appropriate softening agent vapor and then return to a hardened state upon dissipation of the softening agent vapor. The sponge of this type is formed from a high, including a very high, molecular weight polyvinyl alcohol, notably a polyvinyl alcohol having a molecular weight of between approximately 85,000 and 186,000, preferably between approximately 124,000 and 186,000, and most preferably between approximately 160,000 and 186,000.

The polyvinyl alcohol should also be highly hydrolyzed, e.g. greater than 98.0% hydrolyzed and preferably equal to or greater than 99.3% hydrolyzed.

The polyvinyl acetal sponge 18 is formed by reacting the polyvinyl alcohol with formaldehyde in the presence of a catalyst, preferably a mineral acid catalyst such as diluted sulfuric acid, under suitable process conditions. As an example of a suitable process, a quantity of very high molecular weight polyvinyl alcohol which is 99.3% hydrolyzed is initially dispersed in a quantity of deionized water to form an aqueous mixture. A diluted sulfuric acid solution is then stirred into the polyvinyl alcohol aqueous solution and the resulting mixture is blended to thoroughly mix the solutions and to entrain air into the mixture. A formaldehyde solution is then added to the mixture and blending is continued. Optional fillers and excipients such as reinforcing glass bubbles, silica powder, glass beads or glass fibers may be added and blended into the mixture. The mixture is then poured into curing trays of desired width and length and is cured. The resulting cured material shrinks significantly during curing and is then pressure or vacuum washed with water and dried to form the polyvinyl acetal sponge 18. A water repellent may also be applied to the sponge to prevent softening of the sponge upon prolonged exposure to water. A fluorocarbon based water repellent such as 3M Repellent EF-3530 is one example of a suitable repellent. Silicone or wax-based repellents may also be used but are not as preferred.

Depending upon the reaction conditions selected, the polyvinyl acetal sponge 18 has a modulus of elasticity upon bending within the range of 8,000 psi and up to or exceeding 280,000 psi. The sponge 18 preferably has a modulus of elasticity within the range of 132,000 to 172,000 psi, and most preferably approximately 152,000 psi. The sponge density is preferably within the range of 0.49 to 0.87 gm/ml and is most preferably approximately 0.65 gm/ml.

The high strength of the preferred polyvinyl acetal sponge is shown in comparison to polyurethane fiberglass and low temperature thermoplastic splinting material in the following table wherein the specific stiffness is determined by dividing the modulus of elasticity by the specific weight. The equivalent thickness represents the thickness for materials A-E required to attain the same deflection at the same load as the 0.096 inch thick polyvinyl acetal sponge 18, e.g. material E would have to be 0.170 inches thick.

| Synthetic Splinting Material | Modulus of Elasticity (Bending), psi | Density gm/ml | Specific Stiffness $10^6$ inches | Equivalent Thickness inches |
| --- | --- | --- | --- | --- |
| PVAc sponge | 152,000 | 0.65 | 6.48 | 0.096 |
| Low-temp. thermoplastics: | | | | |
| A | 97,000 | 1.24 | 2.16 | 0.112 |
| B | 85,000 | 1.14 | 2.07 | 0.177 |
| Polyurethane/fiberglass: | | | | |
| C | 128,000 | 0.69 | 5.14 | 0.154 |
| D | 115,000 | 0.65 | 4.89 | 0.160 |
| E | 100,000 | 0.54 | 5.14 | 0.170 |

The softening agent vapor 16 is selected from vapors which can be absorbed by sponge 18 to achieve softening thereof but which do not react with the sponge. The softening agent vapors should also exhibit a vapor pressure sufficiently high to permit dissipation of the vapors from the sponge when the sponge is exposed to ambient air at room temperature. Notably, the softening agent vapors selected should provide the desired rate of dissipation yet still provide the desired degree of softening. It has been found that vapors of $C_1$ to $C_3$ alcohols and mixtures thereof provide a particularly suitable balance between the rate of dissipation and degree of softening. Methyl and ethyl alcohols are generally preferred, with anhydrous ethyl alcohol providing the most preferred softening agent vapors. Water vapor may be used as the softening agent vapor in applications where rapid dissipation and a high degree of softening are not needed. A quantity of water vapor may also be mixed with the $C_1$ to $C_3$ alcohol vapors to delay the hardening of the sponge when the $C_1$ to $C_3$ alcohol vapors are used as the primary softening agent vapors. Complete softening of the sponge 18 may be achieved within approximately 4 days when the sponge is saturated with a 95:5 mixture by volume of ethyl alcohol and isopropyl alcohol vapors.

The use of alcohol vapors for softening agent vapor 16 is particularly desirable since such vapors provide a disinfecting environment for the skin surface to which the splint is applied, thereby greatly reducing the risk of infection or maceration of the skin surface. The potential for skin maceration as a result of water contacting the skin for an extended period of time is also eliminated by the use of a vaporous softening agent.

The softening agent vapor 16 is associated with the sponge 18 such as by saturating the sponge with the vapors and then inserting the sponge with associated padding material into and sealing the pouch 12 in an environment saturated with the vapors. Alternately, one or more vials 24 of liquid softening agent are placed into the package to saturate the sponge by providing a saturated vapor environment within the sealed pouch 12. If the liquid softening agent is used, it should be carefully segregated from the sponge to prevent absorption of the liquid by the sponge. Otherwise, the liquid may take an unacceptably long time to dissipate from the sponge following exposure to ambient air. A wicking medium 26 is preferably used to retain the liquid within the vial 24 while permitting the vapors to be released to saturate the sponge 18. As an example of the volume of liquid required to provide a saturated environment within the package, approximately 1.4 cubic inches of ethyl alcohol is used in a package containing a 4" by 15" splint having a ¼" thick sponge 18.

In use, the sealed pouch 12 is opened and the synthetic splint 14 is removed, cut to the desired size and shape as needed, and applied to the body portion, such as an individual's arm or leg. The splint can also be cut while still in the pouch 12 if the fast setting time for the splint limits the time available for cutting and applying the splint.

The splint 14 is applied to the body portion with the padding material 20 placed closest to the skin surface and the splint is hand molded to conform to the contours of the underlying body part. The splint is then wrapped with an elastic bandage or other suitable porous wrap to maintain the splint in place until it has hardened sufficiently. As the softening agent vapors 16 dissipate from the sponge 18, the sponge quickly hardens to initially maintain its shape and then further hardens sufficiently to immobilize the body portion. Notably, the preferred embodiment of the sponge achieves a sufficient hardness to maintain its shape within approximately 2 to 3 minutes following exposure to ambient air and application to the body portion. The applied sponge then reaches a hardness sufficient to immobilize the body portion within approximately 15 minutes of such exposure.

It can thus be seen that the packaged splint 10 is readily available for use by simply removing the synthetic splint 14 from the pouch 12 and applying it directly to the injured body portion. Unlike conventional splints which require that water or a heat source be available to prepare the splint for application to the body portion, the packaged splint 10 of the present invention is ready to use upon removal from the sealed pouch 12. Moreover, the setting process for the sponge 18 does not generate or require the application of heat to the splint so the risk of burning of the underlying skin surface is eliminated.

The sponge 18 is particularly advantageous in that it hardens rapidly as the softening agent 16 dissipates from the sponge so that the splint is self supporting within a matter of as few as 2 minutes and further hardens to immobilize the body portion within as few as 15 minutes. Yet, despite the rapid hardening of the sponge 18, it is readily conformable to the contours of the body portion upon removal from the sealed pouch 12. This conformability increases the effectiveness of the resulting structure and is significantly more comfortable for the patient.

Remarkably, the rapid hardening provided by synthetic splint 14 which contains only a thin layer of polyvinyl acetal sponge 18 has a stiffness which exceeds that of conventional synthetic splints which are much heavier and bulkier than splint 14. For example, the previously described conventional preformed polyvinyl acetal sponge splint which uses steam for softening purposes has a modulus of elasticity of approximately 16,000 psi in comparison to 152,000 psi for the preferred sponge 18 of the present invention and as high as or exceeding 280,000 psi in less preferred embodiments of sponge 18. The reduced weight and bulk of splint 14 and the absence of sharp edges as may be found in conventional splints further contribute significantly to patient comfort. The reduced thickness of the splint also allows it to be readily cut to the desired size and shape prior to application to the body portion. Due to the softness of the sponge 18 and the absence of multiple layers of splinting material, actual application of the splint 14 to the body portion is readily accomplished with a minimal amount of working of the splint to conform to the underlying contours of the body portion.

The packaged splint 10 is also particularly advantageous in that it has an extended shelf life which in general is limited only by leakage of the softening agent vapor 16 from pouch 12. The use of a suitably impermeable pouch 12 may provide a shelf life of up to or exceeding several years.

The present invention is further illustrated in the following example in which the process for making the preferred embodiment of splint 14 is more fully described by way of example and not limitation:

EXAMPLE 1

The proportion of ingredients in the preferred embodiment is as follows:

| Ingredient | Amount |
| --- | --- |
| Polyvinyl alcohol (99.3 + % hydrolyzed) | 50 gm |
| Deionized water | 336 cc |
| Sulfuric acid solution: | |
| Sulfuric acid (95.7% concentration | 64 cc |
| Deionized Water | 265 cc |
| Formaldehyde solution (37% concentration) | 49 cc |

The polyvinyl alcohol (Airvol 165 manufactured by Air Products & Chemicals, Inc., MW = 160,000–186,000) was dispersed at high speed in the deionized water at room temperature. The mixture was then heated in a jacketed container at 80°–85° C. while being stirred at moderate speed. Stirring was continued until the solution was smooth and free of all undissolved particles. The solution was then cooled to 70°–75° C. The sulfuric acid solution at 70°–75° C. was then slowly stirred into the polyvinyl alcohol solution. Stirring was continued and the mixture was cooled down to 18°–22° C. The resulting viscous gray liquid was then dispersed at high speed until it turned completely white and became very tenacious. The temperature was maintained within the range of 18°–22° C. The mixture was then dispersed at 8,000 rpm until the temperature reached 23° C. The formaldehyde solution at 20° C. was then added and dispersing of the mixture was continued until complete mixing was achieved and the temperature reached 23° C. The mixture was then slowly back-stirred to bring any large bubbles to the surface.

The blended mixture was then gently poured into acid resistant trays to a depth of 2½ inches. The trays were maintained at 45° C. for a period of twenty hours. The air velocity around the cure trays was controlled so that the mixture temperature rose from 23° C. to 37° C. within a range of 35 to 85 minutes. The trays were also covered to reduce evaporation of the sulfuric acid solution. The temperature was then increased to 60° C. for four hours. The cured sponges were then removed from the trays, allowed to cool to room temperature, and then cut into ⅜ inch thick slabs and pressure washed with water until the water reached a pH of 6.5 to 7. The washed sponge was then laid out flat on plastic gratings and air-dried for twenty hours with the aid of fans. The air temperature was 22° C.±2° C. and 20% relative humidity±5%.

Upon completion of the air-drying process, the sponges had shrunk to about ½ the width and length dimensions of the original curing trays and ¼ of the original cut thickness. A ¼ inch thick polyurethane foam was then laminated to each sponge using a Silaprene M6587 brand adhesive manufactured by Uniroyal Plastics Company, Inc. The laminated material was then air dried at 22° C.±2° C. and at 20% relative humidity±5% to dry out the adhesive and to reduce the water vapor content of the polyurethane foam. After one to two hours of drying, the laminated material was then cut into the desired widths and lengths.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations.

This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A packaged splint for use in forming a hard structure about a body portion, said packaged splint comprising:
   a layer of polyvinyl acetal sponge made from a polyvinyl alcohol having a molecular weight within the range of approximately 85,000 to approximately 186,000;
   softening agent vapors associated with said sponge for softening the sponge to permit placement thereof about said body portion; and
   a package sealingly enclosing said sponge to maintain the softening agent in association with the sponge, said package being constructed to permit removal of the softened sponge from the package for placement about said body portion, whereupon said sponge sets to a hardened state having a modulus of elasticity within the range of 132,000 to 172,000 psi to form said structure as the softening agent vapors disassociate from the sponge.

2. The packaged splint of claim 1, wherein said sponge is made from a polyvinyl alcohol having a molecular weight within the range of approximately 124,000 to approximately 186,000.

3. The packaged splint of claim 1, wherein said sponge is made from a polyvinyl alcohol having a molecular weight within the range of approximately 160,000 to approximately 186,000.

4. The packaged splint of claim 3, wherein said softening agent vapors are selected from vapors from the group consisting of a $C_1$ to $C_3$ alcohol and water and mixtures thereof.

5. The packaged splint of claim 3, wherein said softening agent vapors are selected from vapors of one or more $C_1$ to $C_3$ alcohols.

6. The packaged splint of claim 3, wherein said softening agent vapors comprise methyl or ethyl alcohol vapors or a mixture thereof.

7. The packaged splint of claim 6, wherein said softening agent vapors comprise ethyl alcohol vapors.

8. The packaged splint of claim 7, wherein said sponge sets to said hardened condition within approximately 15 minutes following removal from said package and exposure to ambient air.

9. The packaged splint of claim 7, wherein said sponge has a density within the range of approximately 0.49 to 0.87 gm/ml.

10. A packaged splint for use in forming a hard structure about a body portion, said packaged splint comprising:
    a layer of polyvinyl acetal sponge made from a polyvinyl alcohol having a molecular weight within the range of approximately 85,000 to approximately 186,000;
    softening agent vapors associated with said sponge and causing softening of the sponge to permit placement thereof about said body portion; and
    a package sealingly enclosing said sponge to maintain the softening agent in association with the sponge, said package being constructed to permit removal of the softened sponge from the package for placement about said body portion, whereupon said sponge sets to a hardened state to form said structure as the softening agent vapors disassociate from the sponge.

11. The packaged splint of claim 10, wherein said sponge is made from a polyvinyl alcohol having a molecular weight within the range of approximately 124,000 to approximately 186,000.

12. The packaged splint of claim 10, wherein said sponge is made from a polyvinyl alcohol having a molecular weight within the range of approximately 160,000 to approximately 186,000.

13. The packaged splint of claim 10, wherein said softening agent vapors are selected from vapors from the group consisting of $C_1$ to $C_3$ alcohol and water and mixtures thereof.

14. The packaged splint of claim 10, wherein said softening agent vapors are selected from vapors of one or more of $C_1$ to $C_3$ alcohols.

15. The packaged splint of claim 10, wherein said softening agent vapors comprise methyl or ethyl alcohol vapors or a mixture thereof.

16. The packaged splint of claim 10, wherein said softening agent vapors comprise ethyl alcohol vapors.

17. The packaged splint of claim 10, wherein said sponge sets to said hardened condition within approximately 15 minutes following removal from said package and exposure to ambient air.

18. The packaged splint of claim 10, wherein said sponge has a density within the range of approximately 0.49 to 0.87 gm/ml.

* * * * *